United States Patent [19]

Stegeman

[11] 4,142,523

[45] Mar. 6, 1979

[54] FLOW CONTROL DEVICE FOR THE INTRAVENOUS ADMINISTRATION OF LIQUIDS

[75] Inventor: Bernardus H. M. J. Stegeman, Zaandam, Netherlands

[73] Assignee: Koninklijke Emballage Industrie Van Leer B.V., Netherlands

[21] Appl. No.: 781,430

[22] Filed: Mar. 25, 1977

[51] Int. Cl.² ............................................. A61M 5/00
[52] U.S. Cl. ......................... 128/214 R; 128/214 C; 128/227; 137/501; 137/613; 222/55
[58] Field of Search .......... 128/214 R, 214 C, 214 E, 128/214 F, 214.2, 227; 222/55; 137/501, 613

[56] References Cited

U.S. PATENT DOCUMENTS

| 3,204,633 | 9/1965 | Hofstra | 128/214 E |
| 3,357,448 | 12/1967 | Martin | 137/501 |
| 3,468,308 | 9/1969 | Bierman | 128/214 F |
| 3,537,475 | 11/1970 | Pottinger | 137/613 |
| 3,642,026 | 2/1972 | Sielaff | 137/859 |
| 4,009,714 | 3/1977 | Hammer | 128/214 C X |
| 4,043,332 | 8/1977 | Metcalf | 128/214 E |

FOREIGN PATENT DOCUMENTS 1269724  4/1972  United Kingdom .................... 137/501

*Primary Examiner*—Dalton L. Truluck
*Attorney, Agent, or Firm*—Stevens, Davis, Miller & Mosher

[57] ABSTRACT

A flow control device for controlling liquid flow, especially a liquid being fed intravenously to a hospital patient. A membrane is deflected in the housing so as to cut off liquid flow when the supply input decreases, thus avoiding the possibility of air being introduced into the system.

9 Claims, 5 Drawing Figures

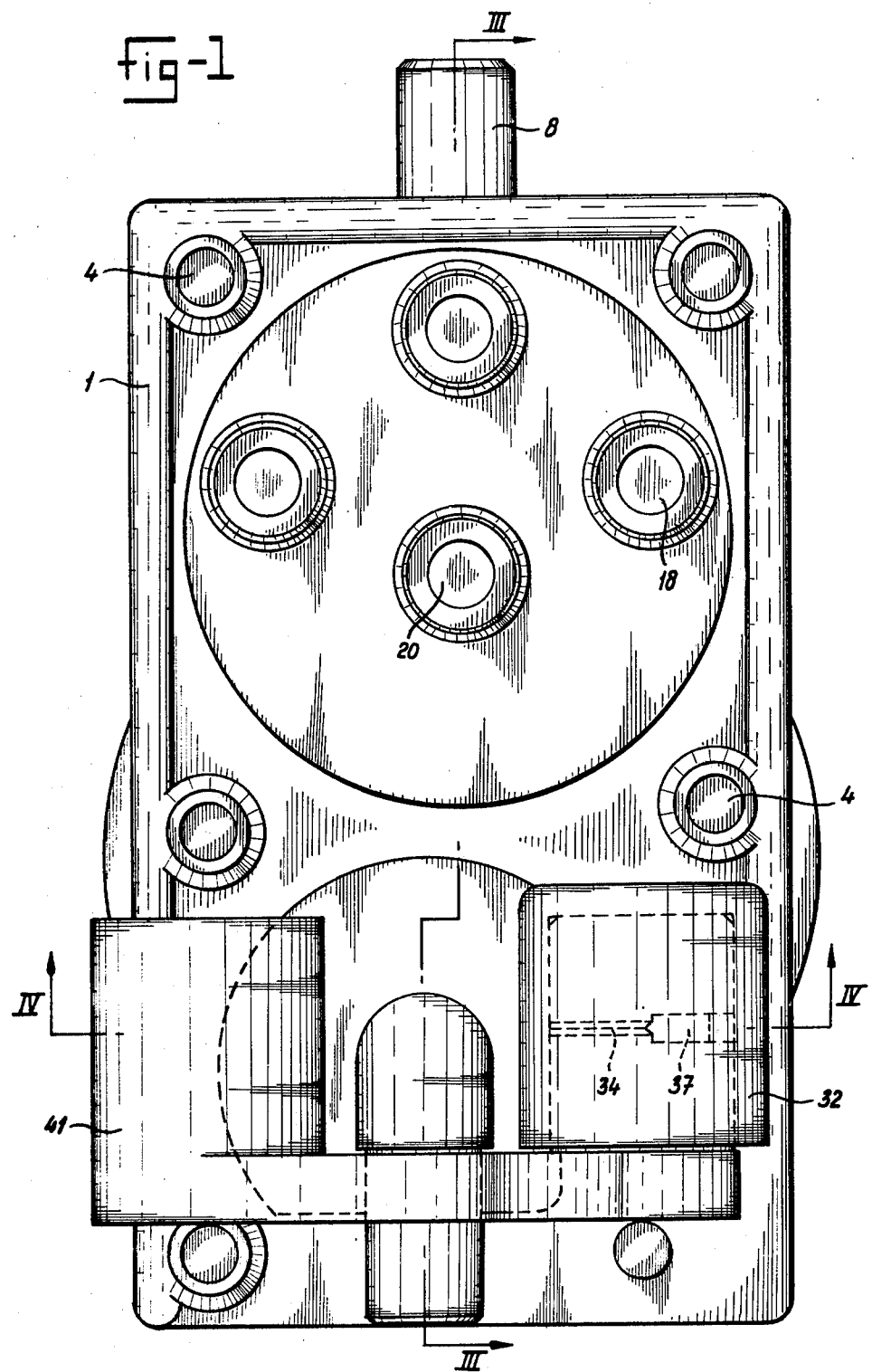

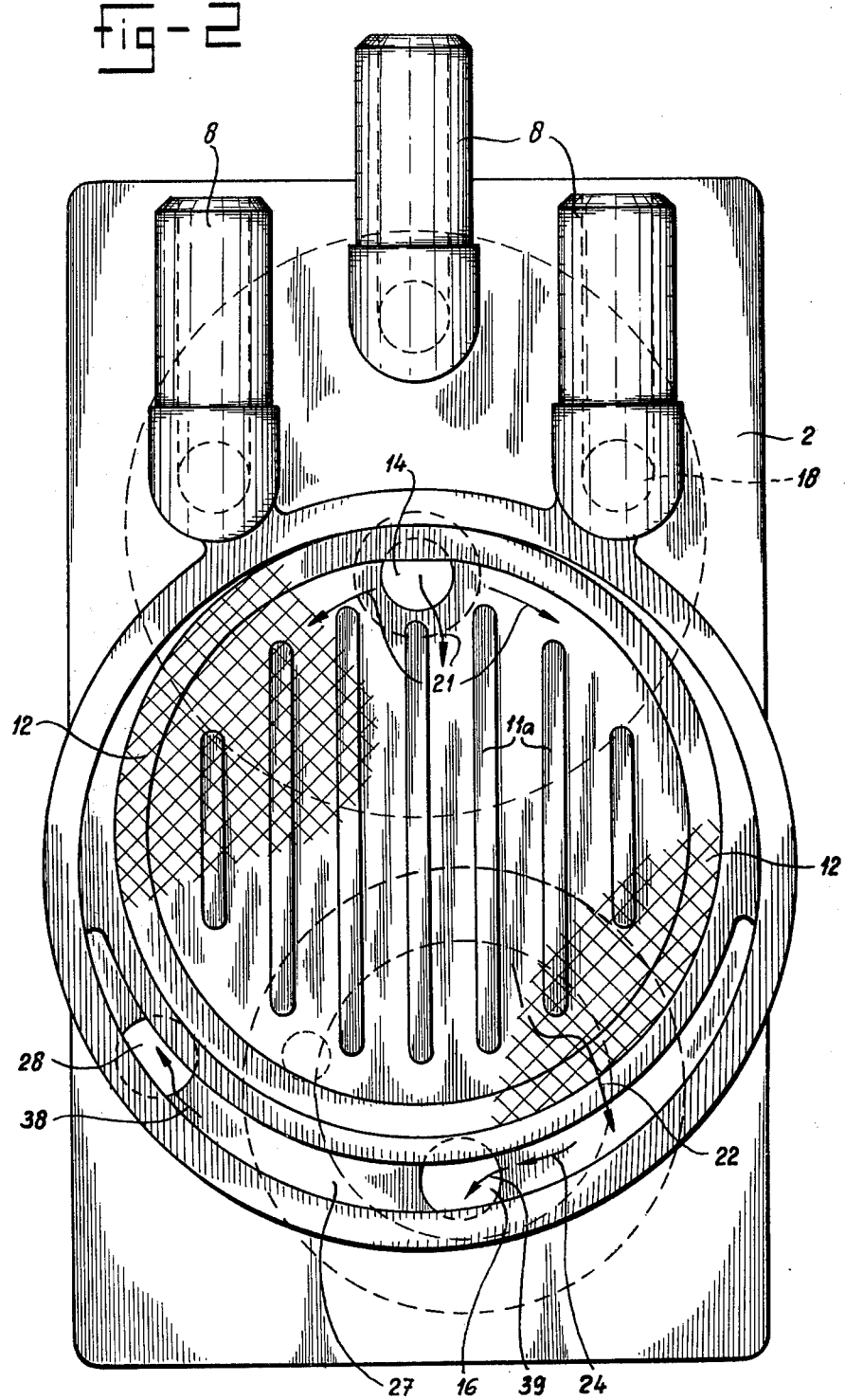

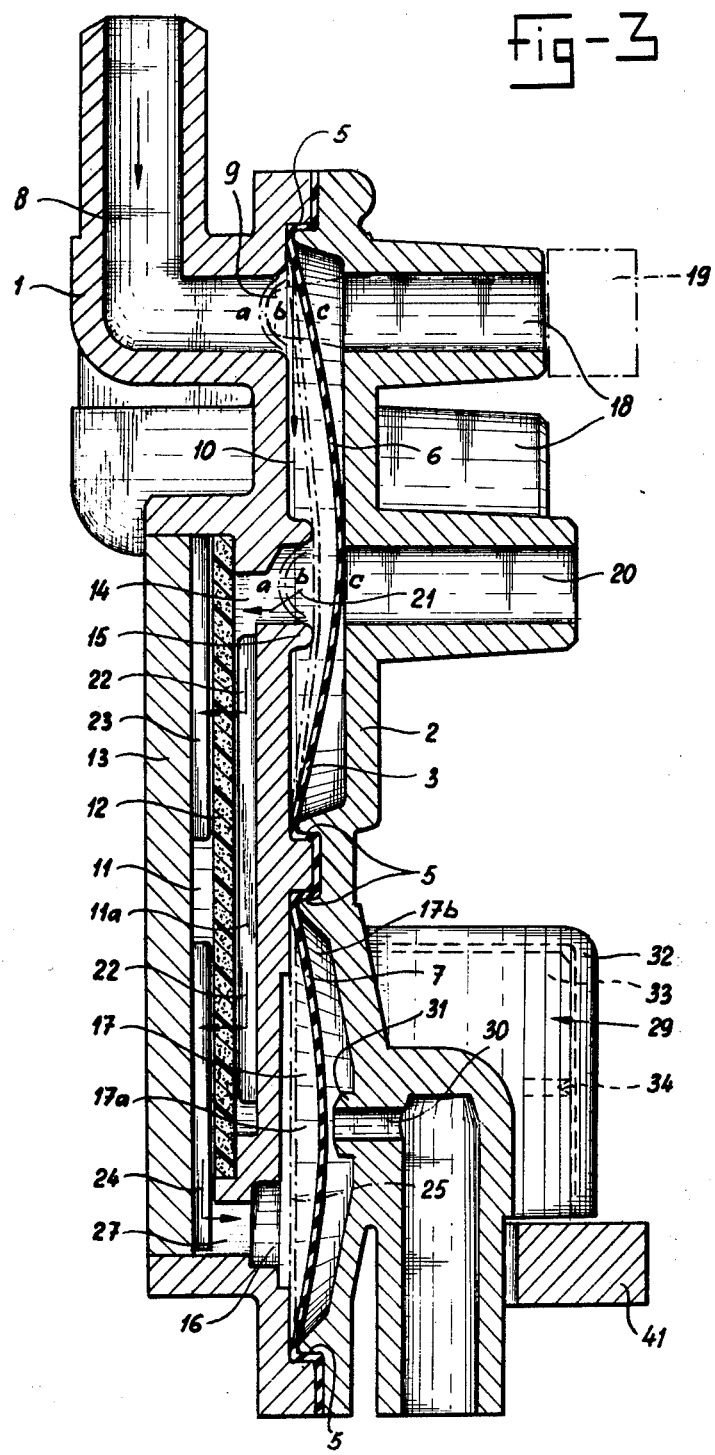

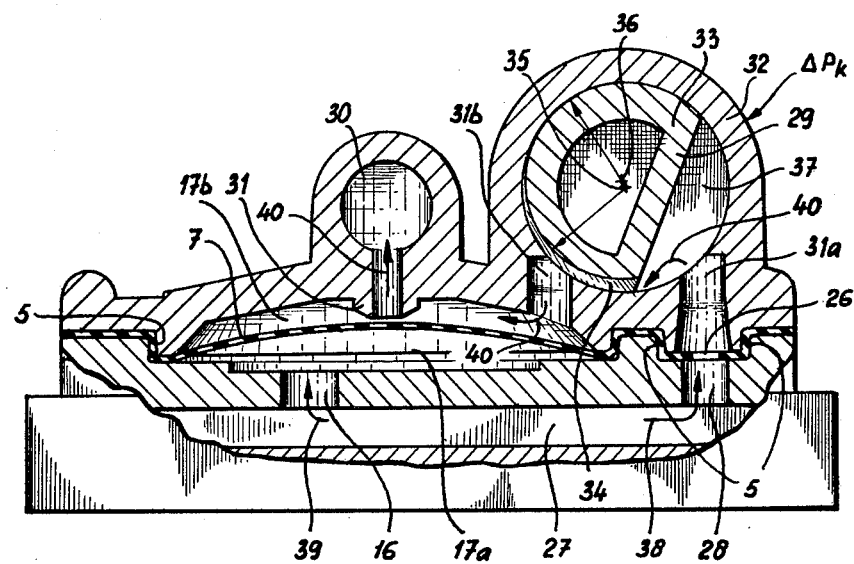
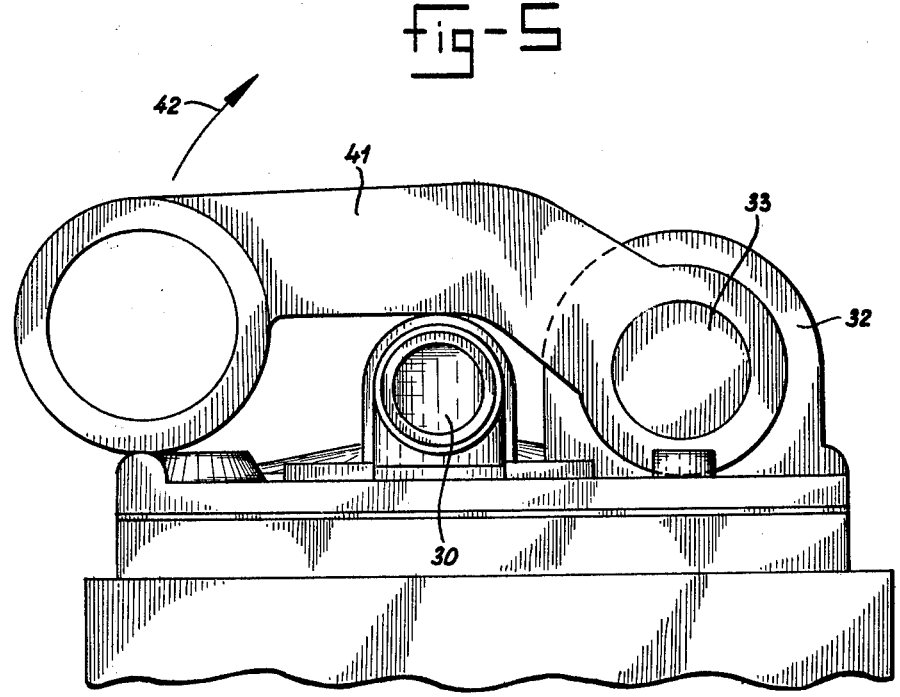

FLOW CONTROL DEVICE FOR THE INTRAVENOUS ADMINISTRATION OF LIQUIDS

This invention relates to a flow control device for example for use in apparatus for the intravenous administration of liquids.

A known intravenous administration apparatus comprises a container for the liquid to be administered, a tube connected to the container, a hollow needle at the end of the tube to be introduced into the vein of a patient, and a device for controlling the quantity of liquid flowing under gravity out of the container to the hollow needle, and is known as a gravity-system. In use the container, such as a bottle or plastic bag, filled with liquid is connected by means of the flexible tube to the hollow needle or canula which is introduced into the vein.

The container is situated at some height above the patient. The flow of liquid is adjusted by means of the control device in the form of an adjustable clamp on the flexible supply tube which includes a drip chamber to give an indication of the rate at which liquid is being administered.

Gravity systems are used for infusion and transfusion. In the case of infusion, liquids such as glucose and salt-solutions, to which medicaments may or may not be added are administered, whereas transfusion is the administration of blood. There is no major difference in the administration techniques and unless otherwise indicated in the following infusion should be understood to include transfusion.

The duration of uninterrupted administration of infusion liquid can vary from some hours to some days, or even longer. The quantity of liquid administered per unit of time is important in particular when some medicaments are added to the infusion liquid.

In case of the existing gravity systems the quantity of liquid administered per unit of time is not very stable, due to the principle and the design of these systems. The main causes of variations ocurring in the adjusted flow rate are changes in:

(a) the flow resistance in the tube near the adjusting clamp and in the hollow needle in the vein,
(b) the resistance to outflow near the end of the needle,
(c) the height of the liquid column in the administration system,
(d) the back pressure of the blood in the vein at the place of the puncture.

Gravity systems continuously require the attention of nursing staff for controlling and readjusting the flow rate and for the timely replacement of the liquid container to prevent air entering the system when the container becomes empty.

More specifically the causes of the above mentioned variations in the adjusted flow rate are as follows:

(a) In the gravity system two constrictions are present, one near the adjusting clamp on the tube and the other in the hollow needle. A third constriction may be present when a micro-filter is included.

The through flow area near the control device is dependent on the adjustment of the device and has a value between 0 and about 0.1 mm². The shape of the flow area in this region of the flow path is an elongated or circular slot with an average opening of the order of microns. Infusion liquids may contain very small solid components which can cause silting up of the control opening by which the flow rate decreases. When a filter is used the same effect can occur with the filter.

A partial clogging of the needle can occur too in particular if the supply of infusion liquid is too slow or there is a back-flow of blood.

A second cause can be unintentional readjustment of the control device. Some systems employ a roll-clamp and other systems a bending-clamp by which a sharp bend is provided in the tube. External causes e.g. movement of the patient, or the visco-elastic properties of the tube material may cause the opening of the slot to vary.

(b) The hollow needle, which is introduced into the vein, has a beveled end whereby the outflow opening is elliptical. The surface of the outflow opening is disposed at a sharp angle to the wall of the vein. Movement of the patient can cause the outflow opening to be restricted by the wall of the vein.

(c) The height of the liquid column in the gravity system affects the flow rate. A change in the height of the liquid column is caused by the decreasing amount of liquid in the container and by any change in the posture of the patient. The height of the liquid column is fixed by the level at which the static pressure in the system above the control clamp is equal to the atmospheric pressure and the relative height of the outflow opening of the needle or canula.

The influence of the drop of the liquid level in the container is at a maximum when there is used a plastic bag or a bottle of the kind to which the air is supplied via an air inlet hose and which has a rubber cap internally provided with an air tube which extends to a position above the level of the liquid in the inverted bottle.

If the interface between the supplied air and the liquid in the system is situated below the liquid level in the container, the effect of the falling liquid level is smaller because the pressure above the liquid falls as the level in the bottle drops.

The maximum pressure variation which can result from a drop in the liquid level in a bottle or bag of 500 cc contents is about 15 cm of water, whereas that which can result from a change in the posture of the patient is about 35 cm of water. Thus the total possible pressure variation is about 50 cm of water.

The change in the height of the liquid column can amount to about 50 cm of water. In consequence of this the liquid pressure can decrease 33–50% in case of an original height of 100–150 cm, resulting in a considerable reduction in the liquid flow rate.

(d) The venous blood pressure is 0–5 cm water column (wc). Any variations have minor influence on the liquid flow rate. When a child is crying, however, the peripheral venous pressure can reach peak values of 100 cm wc. Therefore the average value of the back pressure can vary strongly. Furthermore, the administration system may become clogged by the back flow of blood into the gravity system.

The invention aims to providing a device in which the above mentioned disadvantages are avoided.

In accordance with the invention there is provided a flow control device for controlling liquid flow rate, comprising a supply chamber having an inlet channel, a filter chamber connected to the supply chamber by a passage, and an outlet chamber connected to the filter chamber. A first membrane in the supply chamber is arranged to lie under tension covering the passage between the supply chamber and the filter chamber. There is an inlet channel opening into the supply chamber on the same side of the membrane as the passage, a second membrane in the outlet chamber dividing the chamber into two separate parts connected together by a by-pass channel, and control means for adjusting the through flow area of the by-pass channel. An outlet channel is connected to the part of the outlet chamber downstream of the by-pass channel, the second membrane being movable towards and away from the outlet channel to vary the flow area thereof in accordance with the pressure differential between the two outlet chamber parts.

The flow control device allows adjustment of the liquid flow rate and automatically maintains the adjusted value within narrow limits. Furthermore, the flow control device operates to cut off automatically the liquid flow when the pressure of the liquid in the supply chamber becomes too low, e.g. when a supply container is empty, the pressure on the first membrane being insufficient to hold it clear of the passage between the supply chamber and the filter chamber. This is important if the supply has to be continued and the empty container has to be replaced.

The automatic closing prevents the entry of air into the system because this remains filled with liquid. The replacement of an empty container can take place some time after liquid has stopped flowing from the container which simplifies the task of controlling and replacing liquid containers.

In a preferred embodiment an opening in line with an outlet end of the inlet channel is provided in a wall of the supply chamber on the opposite side of the first membrane to the inlet channel, an element being insertable into the opening to press the first membrane against and thereby close the outlet end of the inlet channel.

The element can be a pin or a remote controlled pressure pin. Further the element can be a pneumatic tube which can be connected to the opening and by means of which the membrane can be pressed with pressurized air against the passage between the supply chamber and the filter chamber.

Preferably the device includes a plurality of supply channels with separate outlet ends and a corresponding number of openings in the opposite wall of the supply chamber, elements being insertable in these openings to open and close selectively the inlet channels. This allows a corresponding number of liquid containers to be connected to the flow control device simultaneously, and the containers can hold the same liquid, such that a prolonged liquid supply is possible without replacing the containers, or the containers can hold different liquids for a mixture of the liquids to be supplied.

In the preferred embodiment a wall of the supply chamber on the opposite side of the membrane to the passage between the supply chamber and the filter chamber has an opening in line with the passage and into which an element can be inserted to press the first membrane into and thereby close the passage.

When the outlet openings of the inlet channels are open and the passage between the supply chamber and the filter chamber is closed, the supply channels form a system of communicating vessels, which can be used for mixing or measuring amounts of liquids. The element can be operated by hand as well as by a remote operating system which can be simply fitted. The particular advantage is that the element does not contact the liquid, so that no connections have to be disengaged and the sterile liquid circuit is not penetrated. Said element can be designed as indicated above. When a pneumatic tube is applied a pulsating pressure can be exerted on the first membrane, such that the membrane can work as a pump.

The control means preferably comprises a cylindrical member rotatable about its axis and having a groove extending around a part of its circumference, the bottom of said groove extending along a circular arc which is eccentric with respect to the axis of the member and the depth of the groove increasing from 0 at one end to 0.5 mm at the other end thereof.

This allows a reliable and simply adjustable control of the flow rate. The groove is preferably V-shaped in cross-section so that in all positions of the cylindrical member the relation between the flow area and the outline of this is as favorable as possible. The optimum shape of the flow area would be a circle, but an approximation to this is a triangle, preferably with an angle of 90°.

Nearly all known control devices have an elongated or circular flow control slot. When the flow area is e.g. 0.1 mm$^2$, the opening of the slot is so small (0.01 mm or less) that solid particles in the liquid will lead to partial clogging of the slot and the flow rate is upset.

An advantage of the preferred embodiment of this invention is that the passage for solid components is at least 10 times larger than in other constructions.

In a transverse plane the groove is semi-circular, the centre of it being eccentric with respect to the axes of the cylindrical member. Experimentally it is established that the flow resistance changes exponentially with the rotation of the cylindrical member by which a very accurate control at low flow rates is possible.

Certain regulations require flow control devices to allow a certain quantity of liquid flow through per unit of time (see e.g. British Standard 2463; 1962, paragraph 33). To meet this requirement it is preferred that the cylindrical member near the end of said groove be provided with a further groove having a flow area which is at least equal to that of the by-pass channel.

A flow control device embodying the invention is described in detail below, by way of example, with reference to the accompanying drawings, in which:

FIG. 1 shows a front elevation of the device;

FIG. 2 shows a back elevation of the device with the filter chamber cover removed and the filter only partially shown;

FIG. 3 is a section taken on the line III—III in FIG. 1;

FIG. 4 is a section taken on the line IV—IV in FIG. 1;

FIG. 5 is an end view of the flow rate control device.

The device shown in the drawings consists of two generally rectangular parts (with dimensions in the range of 2.5 × 5 cm), namely a casing 1 and a cover plate 2, between which a rubber film 3 with a thickness of 0.30 mm is disposed. The casing 1 and the cover plate 2 are clamped together by means of screws 4 which pass through openings in the rubber film which seals between the edges 5 of the casing and the cover and forms two membranes 6 and 7.

The casing 1 has three supply channels 8 having outlet openings 9 connected with a supply chamber 10 and a filter chamber 11. A filter element 12 is installed in the chamber 11 which is closed by a removable filter cover 13, which allows the filter element to be readily renewed or replaced.

Between the supply chamber 10 and the filter chamber 11 is a passage 14, with a protruding rim 15 and a passage 16 connects an outlet chamber 17 to the filter chamber 11.

The cover plate 2 is provided with openings 18 lying opposite the outlet openings 9 of the supply channels 8. In each of these openings an element such as a pin 19 can be inserted to close the related outlet opening 9 partially or completely by pressing the membrane 6 into the outlet opening 9, for example into the position a in which case the outlet opening 9 is completely closed. The cover plate 2 also has an opening 20 lying opposite the passage 14 between the supply chamber 10 and the filter chamber 11 and into which an element can be inserted also to press the membrane 6 into the position a to close completely the passage 14. In a rest position b the membrane 6 lies against the edge 15 under some tension and when liquid under pressure (about 10-15 cm water column) is supplied through a supply channel 8 the membrane 6 is moved into position c. Liquid can then flow through the passage 14 into the filter chamber 11 as indicated by arrow 21, along channels formed by ribs 11a through the filter 12 as indicated by arrows 22 into the grooves formed by ribs 23 on the filter cover 13 and into a groove 27 into which two passages 16 and 28 open.

The outlet chamber 17 contains the membrane 7 which at rest lies in the position 25 indicated by a chain dotted line and which divides the outlet chamber into closed part 17a and a part 17b to which an outlet channel 30 is connected.

As indicated in FIG. 4 the groove 27 is connected to the part 17a of the chamber 17 by the passage 16 and to the part 17b of chamber 17 by the passage 28, an opening 26 in the rubber film, and a by pass channel 31a, 31b.

Around the outlet opening 30 a rim 31 is formed. When the pressure of the liquid flowing out of the filter chamber is higher than the pressure in the outlet channel 30 the membrane 7 moves towards the rim 31 and the membrane 7 closes the channel 30 partially or completely.

A control arrangement 29 divides the by-pass channel into two parts 31a and 31b defined in a casing 32 in which a cylindrical pin 33 is sealingly located. The pin 33 has a groove 34 which groove extends over a part of the circumference in a plane perpendicular to the pin axis, and the bottom of the groove describes a circular arc with its centre 35 lying eccentric with respect to the centre 36 of the circular section of the pin 33. The cross section of the groove is triangular preferably with an apex angle of 90°. A further groove 37 is provided in the pin and is connected to the groove 34 at its deeper end.

Liquid flowing out of the filter chamber as indicated by arrow 24, divides into two portions (arrows 38 and 39). One portion (arrow 38) flows to the outlet channel 30 (arrows 40) and the other portion (arrow 39) exerts a pressure on the side of the membrane 7 remote from the outlet channel 30.

The groove 37 ensures that a certain quantity of liquid will flow through per unit of time as is required by British Standards 2463; 1962, paragraph 33. A similar requirement applies in various other countries also.

The adjustment of the groove 34 with respect to the by-pass channel part 31b is achieved by means of a lever 41 attached to the pin 33 and rotatable as indicated by the arrow 42. This adjustment alters the liquid flow rate through the device.

One or more channels 8 are connected to liquid containers by means of flexible tubes. The outlet channel 30 is connected to a further flexible tube, the other end of which is provided with a hollow needle or canula which can be introduced into the vein of a person to which the liquid is to be administered. In this further tube a drip chamber is interposed.

The liquid flowing to the supply channel 8 displaces the membrane 6 from the position b to the position c if the pressure is sufficient. Then the liquid flows via the passage 14 according to the arrows 21, 22 and 24 to the groove 27 and is divided there as indicated by the arrows 38 and 39. The liquid flowing according to the arrow 38 enters the first part 31a of the by-pass channel 31a, 31b the desired through flow quantity being adjusted by positioning the groove 34 and subsequently flows to the outlet channel 30 as indicated by the arrows 40. The liquid diverted according to the arrow 39 exerts a pressure on the membrane 7 by which the membrane 7 is moved towards the rim 31. As a result the pressure drop across the partially closed opening of channel 30 is controlled and the pressure drop across the control arrangement 29 is kept constant so that the liquid flow rate remains constant. If before it is used the device is sterile, during its use those parts through which the liquid flows or is present remains sterile because the device remains completely sealed.

It will be clear that the flow control device is completely automatic. If the liquid pressure in the container becomes too low, the membrane 6 will engage the edge 15 and the supply of liquid is interrupted. The liquid flow rate is adjusted by the flow control arrangement and is automatically maintained constant by the membrane 7.

A number of containers containing liquid to be administered can be connected to the device. When the containers contain the same liquid administration to the patient can take place for a long period without interruption. When the containers are filled with different liquids to be administered as a mixture to the patient, it is possible to do this by hand by adjusting the pins 19 or e.g., by means of a device which operates according to a fixed system which can be remote controlled. The latter might be automatically carried out in a simple way according to a fixed program.

The described device can be used in other fields besides administering liquids to patients. Indeed, it could be used in any application where small quantities of a liquid have to be dispensed at fixed rates, such as e.g. in chemical processes, preparing of drinking-water, etc.

The described control device can achieve the following advantages when used in a transfusion or infusion set:

(a) Saving in labor of nursing staff, particularly since the time between the replacement of the liquid containers can be 200% of that in the case of known devices;

(b) Improved safety, due to a better controlled administration of medicaments added to the liquid;

(c) Augmentation of the technical possibilities in case of intravenous therapy with retention of the condition that an administration system can be used which is used only once. The action of the connection of a remote control system is limited to putting in pin-shaped elements in the above mentioned openings in that side of the supply chamber of the flow control device which is turned away from the filter. The possibility of independent control of the liquid connections in combination with a constant liquid flow rate makes it possible to compose in-process a mixture of a number of liquids or liquid-compositions. This takes place by controlling each of the connections in cyclic sequence on different points of time and during short periods. By this every mixture ratio can be obtained. The mixture ratio can be constant or variable (by means of a program). A feedback system to the patient is also conceivable from a technical point of view.

What I claim is:

1. A flow control device for controlling the liquid flow rate during an intravenous administration comprising a housing defining a supply chamber having an inlet channel means, a filter chamber connected to the supply chamber by a passage means; an outlet chamber connected to the filter chamber; a first membrane in the supply chamber arranged to lie under tension covering the passage means between the supply chamber and the filter chamber means, the inlet channel opening into the supply chamber on the same side of the membrane as the passage means; a second membrane in the outlet chamber dividing the chamber into two separate parts; a by-pass channel means connecting said separate parts; control means for adjusting the through flow area of the by-pass channel means; an outlet channel means connected to the part of the outlet chamber downstream of the by-pass channel means, the second membrane being movable towards and away from the outlet channel means to vary the flow area thereof in accordance with the pressure differential between the two outlet chamber parts.

2. A device according to claim 1, including an opening in the housing in line with an outlet end of the inlet channel means of the supply chamber and on the opposite side of the first membrane to the inlet channel means, an element insertable into the opening to press the first membrane against and thereby close the outlet end of the inlet channel means.

3. A device according to claim 2, wherein a plurality of inlet channel means connected to the supply chamber and a corresponding number of openings are provided in the opposite wall of the supply chamber in line with the outlet ends of the inlet channel means.

4. A device according to claim 1, wherein a wall of the supply chamber on the opposite side of the membrane to the passage means between the supply chamber and the filter chamber has an opening in line with the passage means and into which an element can be inserted to press the first membrane into and thereby close the passage means.

5. A device according to claim 1, wherein the control means comprises a cylindrical member rotatable about its axis and having a groove extending around a part of its circumference, the bottom of said groove extending along a circular arc which is eccentric with respect to the axis of the member and the depth of the groove increasing from 0 at one end to 0.5 mm at the other end thereof.

6. A device according to claim 5, wherein the groove is V-shaped in cross-section.

7. A device according to claim 5, wherein the cylindrical member is provided with a further groove with a flow area which is at least equal to that of the by-pass channel means.

8. The device of claim 1 which is arranged generally lineally with the inlet channel means at one end and the outlet channel means at the other end and the first and second membranes extending generally parallel to the longitudinal axis of the housing so as to facilitate liquid flow therethrough.

9. The device of claim 8 in which the housing is generally vertically extending.

* * * * *

UNITED STATES PATENT AND TRADEMARK OFFICE
CERTIFICATE OF CORRECTION

PATENT NO. : 4,142,523
DATED : March 6, 1979
INVENTOR(S) : Bernardus H. M. J. Stegeman It is certified that error appears in the above—identified patent and that said Letters Patent are hereby corrected as shown below:

After Item"[22] Filed  Mar. 25, 1977" please insert
---[30]  Foreign Application Priority Data
       March 31, 1976    Netherlands.......... 76.03356--

Signed and Sealed this

Tenth Day of July 1979

[SEAL]

Attest:

LUTRELLE F. PARKER

*Attesting Officer*    *Acting Commissioner of Patents and Trademarks*